United States Patent [19]
Strauss et al.

[11] Patent Number: 6,159,163
[45] Date of Patent: Dec. 12, 2000

[54] SYSTEM FOR ATTENUATING PAIN DURING BONE MARROW ASPIRATION AND METHOD

[75] Inventors: Jonathan S. Strauss, Los Angeles; Christopher L. Felten, Northridge, both of Calif.

[73] Assignee: Cedars-Sinai Medical Center, Los Angeles, Calif.

[21] Appl. No.: 09/074,258

[22] Filed: May 7, 1998

[51] Int. Cl.⁷ ................................................. A61B 10/00

[52] U.S. Cl. ............................ 600/566; 604/170; 607/99

[58] Field of Search ...................... 607/99, 116; 604/167, 604/170; 600/566, 564, 565

[56] References Cited

U.S. PATENT DOCUMENTS

| | | |
|---|---|---|
| 2,866,461 | 12/1958 | Suzuki . |
| 4,411,657 | 10/1983 | Galindo . |
| 4,469,109 | 9/1984 | Mehl . |
| 4,683,896 | 8/1987 | Herbst et al. . |
| 5,306,236 | 4/1994 | Blumenfeld et al. ................... 607/116 |
| 5,366,489 | 11/1994 | Burgio et al. . |
| 5,433,739 | 7/1995 | Sluijter ...................................... 607/99 |

FOREIGN PATENT DOCUMENTS

6918370  6/1970  Netherlands .

OTHER PUBLICATIONS

Article "Electronic Dental Anesthesia: A Pilot Study,", by Carmine J. Esposito, Jeffrey S. Shay and Ballard Morgan, Quintessence International, vol. 24, No. 3/1993, pp. 167–170.

Article "Electronic Anesthesia For Primary Molar Restoration In A 27–Month–Old Child: A Case Report,"by Theodore P. Croll, Quintessence International, vol. 26, No. 8/1995, pp. 549–551.

Article "An Introduction To Dental Electronic Anesthesia," by Adrian U J. Yap and G. Ong, Quintessence International, vol. 27, No. 5/1996, pp. 325–331.

*Primary Examiner*—Cary O'Connor
*Assistant Examiner*—Pamela Wingood
*Attorney, Agent, or Firm*—Pretty, Schroeder & Poplawski

[57] ABSTRACT

A biopsy sampling system and method for aspirating bone marrow and bone cores from a patient with minimal or no perceived pain to the patient. The system includes a bone aspiration needle assembly having a handle and an electrically conductive needle shaft and an electrical nerve stimulator (ENS) which supplies a current of adjustable intensity to the needle shaft. Thus, when the aspirating needle is inserted into the bone marrow cavity of the patient, the stimulator is activated to anesthetize the nerves in the vicinity of the aspiration permitting the extraction to commence with little or no increased pain to the patient. A nonconducting insulating shaft is also disclosed to be placed on the needle shaft in order direct the ENS current to the area of the shaft that can most efficiently anesthetize the pain conducting nerves, i.e. to the tip of the needle shaft.

17 Claims, 4 Drawing Sheets

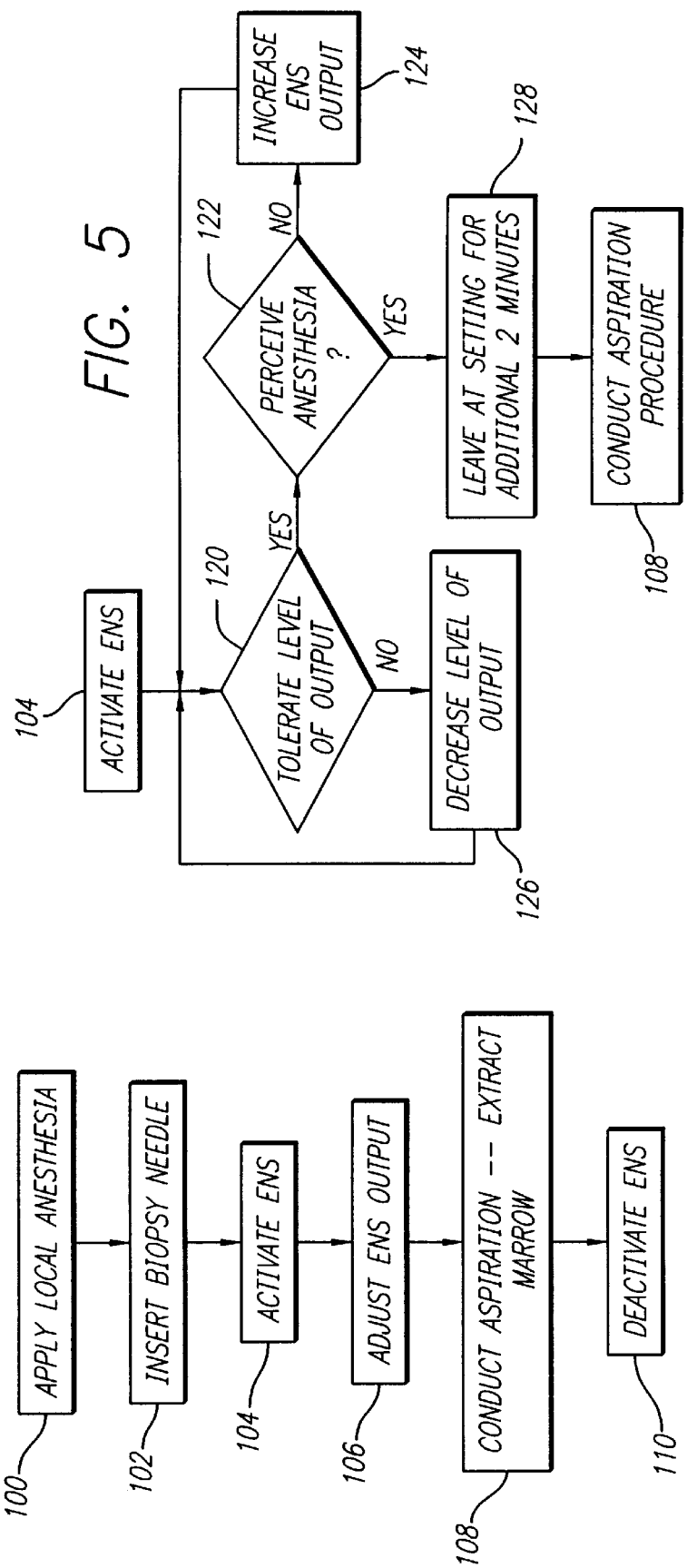

SYSTEM FOR ATTENUATING PAIN DURING BONE MARROW ASPIRATION AND METHOD

BACKGROUND OF THE INVENTION

1. Field of the Invention

This invention relates generally to bone marrow aspiration and biopsy procedures and more particularly to a device and procedure for attenuating the pain associated with such procedures.

2. Description of the Related Art

In order to diagnose the presence of numerous blood-related diseases, such as blood infections, leukemia and other malignancies, and the cause of blood abnormalities, such as anemia, hematologists often examine the bone marrow of their patients. Two types of specimens are often removed from a patient for analysis. In one procedure, bone marrow is extracted, or aspirated, from the cavity of a bone. In a second procedure, one or more pieces of bone, called "core biopsies," or "bone plugs," are also removed for diagnosis. The entire process typically lasts anywhere from ten to thirty minutes, depending on numerous factors, including the amount of marrow needed, the difficulty of positioning and inserting the needle, the hardness of the bone, the experience of the physician, etc.

These two procedures are often performed in succession. First, a specialized, biopsy needle having a removable trocar, or stylet, fully inserted into the needle lumen is inserted into and through an appropriate bone structure of the patient, such as the posterior iliac spine (i.e. pelvic bone) or sternum, and into the bone marrow cavity. The trocar is removed and an appropriate method for aspirating the desired amount of marrow tissue into the needle lumen is used. Aspiration may be accomplished by rapidly retracting the plunger of an attached syringe thereby creating a upward, suction force, by employing an aspirator bulb, or by another method known in the art.

In order to perform the subsequent procedure, the needle is typically retracted a few millimeters until it exits the bone structure from which the marrow was aspirated. Then, the needle is reinserted, this time without the trocar inserted in the lumen, into a neighboring area of the bone in order to effectively core out a piece of bone into the lumen for removal and analysis. The physician often needs to apply a considerable amount of force when coring the bone plug.

Both the aspiration and coring procedures can cause significant discomfort and pain to the patient. First, the insertion of the needle through the skin, subcutaneous tissue and muscle tissue usually causes moderate pain. Further, as the needle passes through the bone, a strong, pressure-like sensation is experienced. The part of the aspiration procedure causing the most pain, however, is the actual aspiration action. This pulling sensation, which lasts as long as the syringe plunger is retracted, has been described by some as agonizingly painful, while others perceive less intense pain, depending on the patient's pain threshold and level of apprehension and fear. Further, while the bone coring procedure has not been described as acutely painful as the aspiration procedure, it does cause moderate to severe discomfort. Accordingly, it has been a goal of medical practitioners to find ways to ameliorate the discomfort and pain associated with these procedures.

The injection of local anesthesia, such as lidocaine, prior to these procedures, is effective in desensitizing soft tissue and the bone surface, or periosteum, to be pierced. Unfortunately, local anesthesia cannot anesthetize the inside of the bone and thus is ineffective to reduce the pain associated with the aspiration and coring actions.

While the use of general anesthesia would, of course, be expected to eliminate the perceived pain, it is not commonly used for these procedures due to the risks related to general anesthesia. As an alternative, some physicians elect to prescribe a benzodiazepine or another mild tranquilizer for patients having a high degree of apprehension prior to these biopsy procedures. However, no known viable and completely safe procedure presently exists to eliminate or significantly reduce the pain associated with the aspiration and coring steps of these procedures. Thus, the bone marrow aspiration and coring procedures have continued to cause a great deal of anxiety, discomfort and pain in many patients of all ages who must undergo them.

Accordingly, it should be appreciated that there exists a definite need for an improved product and method which tends to significantly reduce or eliminate the pain associated with the aspiration and bone coring steps of the conventional bone marrow procedure.

SUMMARY OF THE INVENTION

The present invention, which addresses this need, is embodied in an apparatus and method which directly applies electrical nerve stimulation to the vicinity of the bone structure and marrow to be aspirated and bone to be cored. A low level electric current is applied to the biopsy needle that has been inserted into the bone structure. In this way, the electrical nerve stimulation is directly introduced into an area that cannot be reached with the electrode pads of conventional transcutaneous electrical nerve stimulator systems. This treatment tends to significantly reduce the discomfort and pain which is otherwise experienced during the aspiration procedure and that cannot be effectively and safely attenuated with local anesthesia or other pain management procedures or medication.

In particular, the biopsy sampling system of the present invention includes an electrically conductive biopsy needle that extracts the sample; and an electrical nerve stimulator in communication with the needle, the stimulator being configured to supply an adjustable current to the needle to attenuate the pain during the extraction. More particularly, the electrical nerve stimulator includes an adjustable energy delivery source, a first electrode in communication with the needle and a second electrode having a free end that removably engages the skin of the patient. The needle includes a handle having a plug receptacle that receives the first electrode of the electrical nerve stimulator and an electrically conductive needle shaft having one end connected to the handle and in communication with the plug receptacle and an opposite, free end adapted to bore the bone of the patient.

In more detailed aspects of the present invention, the electrical nerve stimulator further includes a skin patch or pad connected to the second electrode of the stimulator. This patch is designed to be placed on the skin of the patient near the insertion point of the needle shaft into the patient and serves to complete the electrical circuit.

In operation, the aspiration method of the present invention includes penetrating the needle shaft of the biopsy needle assembly into the bone structure within the patient, activating the electrical nerve stimulator to supply an initial controllable electrical current to the needle shaft, gradually increasing the electrical current supplied by the electrical nerve stimulator to a desired magnitude, maintaining the supply of current for a preset period of time, extracting the sample from the patient into the biopsy needle assembly, and then deactivating the electrical nerve stimulator.

In a more detailed feature of the invention, designed to further focus the current flow from the stimulator to the area of the bone and marrow to be aspirated and/or cored, an electrically insulating sheath envelops a portion of the needle shaft and extends from the needle handle for a distance less than the length of the needle shaft. In this way, the current that travels down the inserted needle shaft is directed to the tip of the needle shaft, that is, the area surrounded by the nerve fibers that transmit the pain signals associated with aspiration. In yet another embodiment, a slidable electrically insulating sheath envelops a portion of the needle shaft and extends from the needle handle for a distance less than the length of the needle shaft, so that the needle can be fully inserted into the bone of the patient while the sheath remains completely outside of the patient. Once the needle is in place within the patient, the sheath is slid down the shaft and into the patient's soft tissue. This provides the advantage of permitting a biopsy needle, unencumbered by a sheath, to enter through the patient's tissue and bone, thus reducing the risk that portions of the sheath will fray or shear off into the patient.

Other features and advantages of the present invention will become more apparent from the following description of the preferred embodiments, taken in conjunction with the accompanying drawings, which illustrate, by way of example, the principles of the invention.

BRIEF DESCRIPTION OF THE DRAWINGS

FIG. 4 is a flow chart describing the steps of an aspiration procedure performed according to the present invention;

FIG. 5 is a flow chart describing the step of increasing the nerve stimulator shown in FIG. 4 in greater detail;

FIG. 7b is a cross-sectional side view of the device shown in FIG. 7a.

DETAILED DESCRIPTION OF THE PREFERRED EMBODIMENTS

The invention summarized above and defined by the enumerated claims may be better understood by referring to the following detailed description, which should be read in conjunction with the accompanying drawings. This detailed description of particular preferred embodiments, set out below to enable one to build and use those particular implementations of the invention, is not intended to limit the enumerated claims, but to serve as particular examples thereof. The particular examples set out below are the preferred specific implementations of an improved aspirating needle, namely, one that carries an electrical current of a selectably variable magnitude into the medullary space in order to reduce the discomfort and pain associated with aspiration action. The invention, however, may also be applied to other types of systems and equipment as well.

Before describing the invention in further detail, it will be helpful to provide background information relating to the application of electrical nerve stimulation for the purpose of reducing pain in the mammalian body.

I. Transcutaneous Electrical Nerve Stimulation ("TENS")

Transcutaneous electrical nerve stimulation, or TENS, is a well known physical therapy technique for the relief of pain. Conventionally, with TENS, low level electrical stimulation is directed to chronic pain areas via surface electrode pads, and the current passing through these areas reduces or eliminates the perceived pain. Recently, this principle has been successfully applied as a noninvasive form of dental anesthesia to block pain caused by a variety of dental procedures.

The theory underlying TENS is that electrical stimulation of the large beta nerve fibers for pressure and touch produces impulses that conduct faster than along the smaller, "A delta" and "C pain" fibers. Thus, the nerve impulses of the pressure and touch fibers arrive at the spinal cord before the pain impulses and effectively "close the gate," thereby suppressing the pain. It is also thought that the electrical stimulation causes some nerve cells to produce local beta-endorphins causing local anesthesia. In addition, serotonin may be released systemically, increasing the patient's threshold for pain.

As its name implies, electrical anesthesia via the application of TENS has been typically accomplished transcutaneously. That is, the anesthetizing electricity has been directed to the area to be treated by traveling across the surface of the skin via electrode pads stuck to the skin. However, electrical anesthesia has not been commonly applied percutaneously, that is, by physically introducing a stimulating electrode inside the body and applying the electricity directly to the affected area.

II. Aspiration and Method of Employing Electrical Anesthesia Thereto

Figure 1:
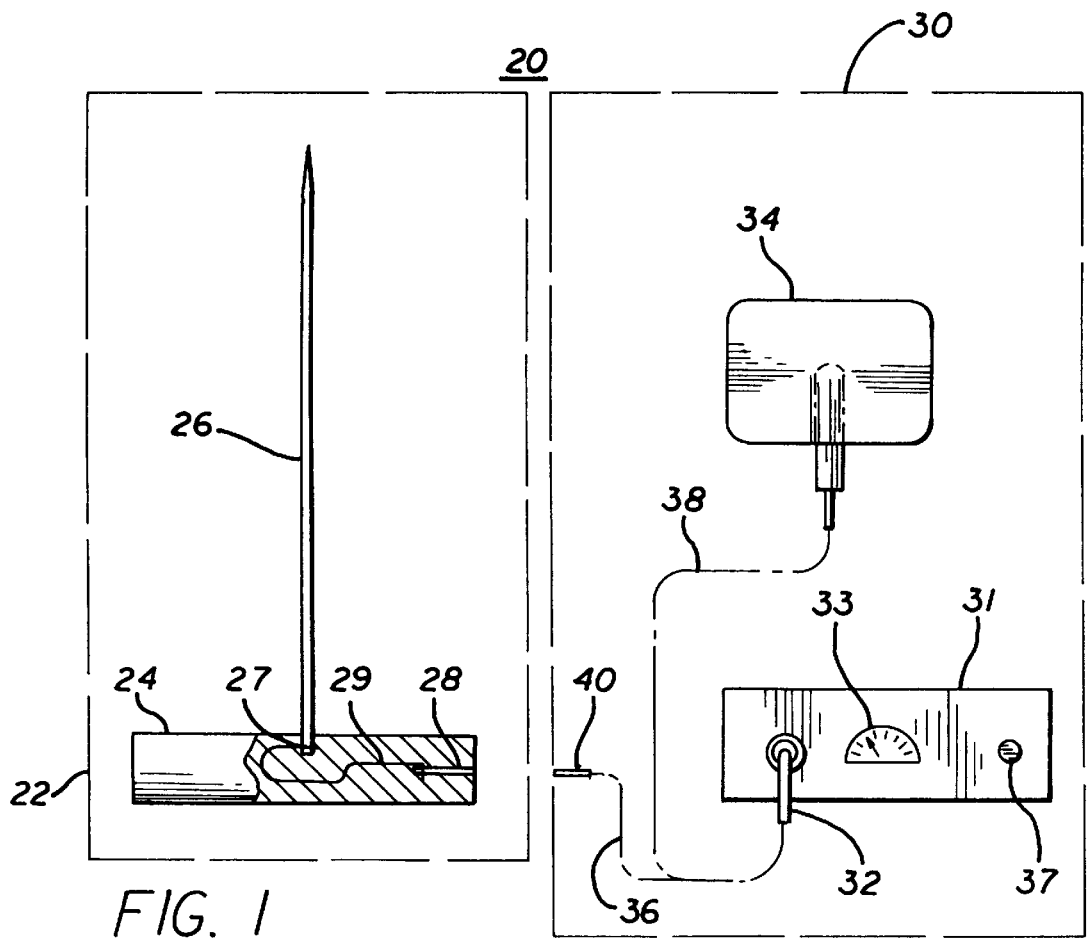
FIG. 1 illustrates the basic components of the biopsy sampling system of the present invention.

Referring now to the figures, FIG. 1 illustrates the basic components of the biopsy sampling system 20 of the present invention. A biopsy needle 22, often called a Jamshidi® needle, includes a handle 24 and an aspirating needle shaft 26. The handle 24 includes a plug receptacle 28, which is associated with the needle shaft 26 by being electrically connected to the first end 27 of the needle shaft 26 via a conductor 29. The nerve stimulator 30 includes a current generator, or electrical nerve stimulator (ENS) generator, 31 having an adjustable output controller 37 and an electrode pair 32 comprising a first electrode 36 and a second electrode 38. In this example, the first electrode 36 the negative electrode and terminates in a plug 40 for mating with the plug receptacle 28 of the needle 22. The second electrode 38 is the positive electrode and terminates in an electrode pad, or patch, 34 to be placed on the skin surface of the patient near the point of insertion of the needle shaft 26. Conventional conducting surface electrode pads may be used and are well known in the art. However, it is understood that the polarity of the first and second electrodes may be reversed and that any of a variety of acceptable methods of electrically connecting the first electrode 36 to the electrically conducting needle shaft 26 may be used. As discussed further below, when the components of the system 20 are connected, the generator 31 is powered, and the needle 26 is in place inside the patient's bone structure, the completed anesthetizing electrical circuit carries current from the generator 31 to the first electrode 36, through the handle 24 and down the needle shaft 26 to its tip, through the patient's body to the electrode pad 34 and finally back to the generator 31.

The generator 31 also includes an ammeter 33 for displaying the magnitude of the current supply to the patient during the procedure. The meter 33 enables the physician to monitor the current flowing through the patient while adjusting (increasing) the output voltage to ensure that the current does not exceed a set limit for a given patient. An upper current limit may be determined for a particular patient the first time he or she undergoes this procedure. In particular, the attending physician records the amperage displayed at the maximum stimulating output at which the patient perceives anesthesia without attendant pain. This is described more fully below with reference to FIG. 6. Should that patient require one or more future bone marrow aspiration procedures, a record of the maximum recommended amperage for that patient now exists and the physician easily can monitor that current flow on the generator 31.

Figure 2:
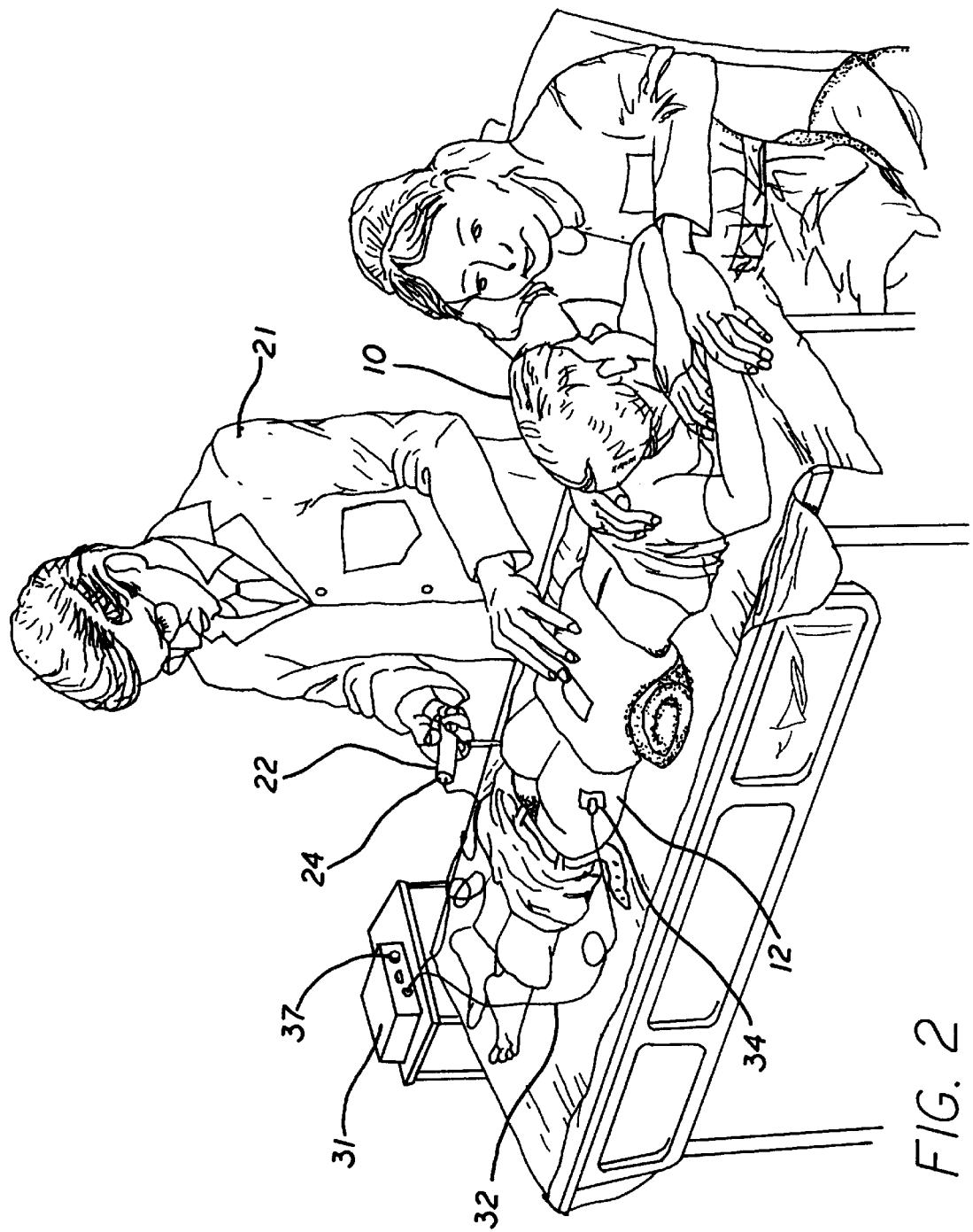
FIG. 2 is an illustration of a bone marrow aspiration-biopsy procedure performed on a patient using the biopsy sampling system of the present invention.

Referring to FIG. 2, a typical bone marrow aspiration/biopsy procedure using the biopsy sampling system of the present invention is shown. In this example, a medical specialist 21 conducts the procedure in the iliac spine region 12 of a child patient 10. As is conventionally done, the specialist 21 firmly holds the biopsy needle 22 by its handle 24, and inserts the needle shaft through the skin and muscle tissue and into the child's iliac spine 12. As shown, the electrical nerve stimulator generator 31 is electrically connected to the needle 22 at its handle 24 and the electrode patch 34 is applied to the patient's skin near the point of needle insertion.

Figure 3:
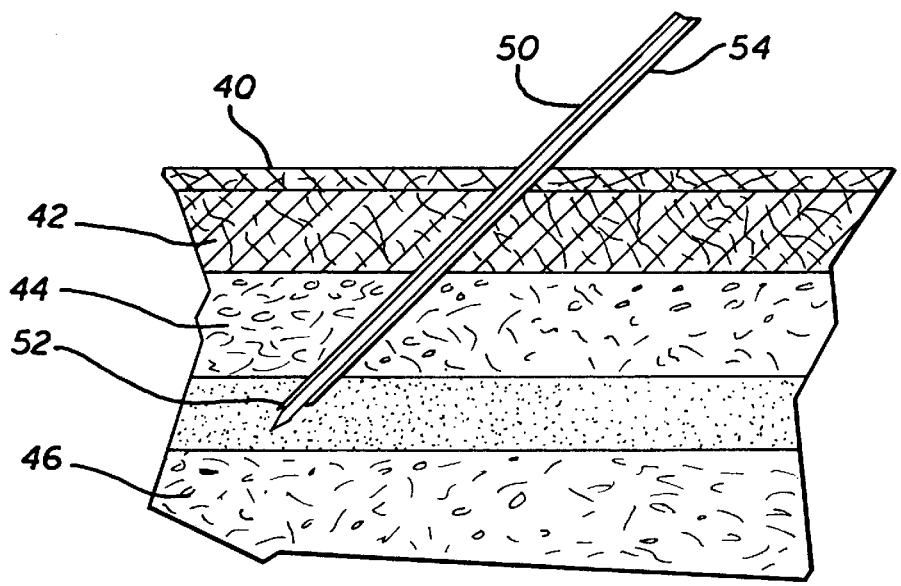
FIG. 3 is a cross-sectional view of the portion of the biopsy needle shaft of the present invention inserted into the bone cavity of a patient.

FIG. 3 details a portion of the needle 22 while the needle shaft 26 is inserted in the patient. In particular, the needle shaft 26 includes an electrically conductive cannula 50 having a free end 52 and a trocar 54 inserted in the lumen of the cannula 50. The needle shaft 26 passes through the epidermis 40, soft tissue 42 and with considerable force, through the bone 44 (in this example, the iliac crest) and into the medullary cavity 46 containing the marrow to be aspirated.

The method that a specialist, such as the physician depicted in FIG. 2, employs according to the present invention is now described. The inventors of the present invention have found that applying electrical stimulation into the bone tissue, close to the location of the marrow to be extracted, for a few minutes prior to and during the drawing of the marrow, tends to significantly attenuate the pressure-like and painful sensations associated with the aspiration step. Experimentation has shown that after the biopsy needle is inserted in the bone cavity, the application of a gradually increasing electric current of the type often used in dental anesthesia, such as the output from a BioMed 2000 Transcutaneous Stimulator (BioMedical Life-System, Vista, Calif.), set in continuous mode at a pulse rate between 35 to 135 and pulse width of 160, to the area to be aspirated for approximately 10 minutes, significantly attenuates the pain and discomfort during the actual aspirations.

Accordingly, FIG. 4 depicts the steps undertaken in a typical marrow aspiration procedure according to one preferred embodiment of the present invention. As is conventionally done prior to the procedure, the physician injects, in step 100, a local anesthesia, such as lidocaine, into the patient to numb the general area to be pierced. Then, in step 102, the biopsy needle is inserted into the patient, as was described with reference to FIG. 3. Once the needle is in place, the electrical nerve stimulator (ENS) generator 31 is turned on at a relatively low frequency and voltage level, step 104, causing electrical energy, or current, to travel along the length of the conductive cannula 50. Prior to aspiration, the output voltage of the stimulator is gradually increased until anesthetic effect is achieved, step 106, and is left on at this increased level for an appropriate period of time. As previously discussed, this step stimulates the nerves in the vicinity of the energized cannula, including the pain transmitting nerves, so that the pain signals resulting from the aspiration are attenuated. During experimentation, a stimulating time of approximately ten minutes was used and found to be effective. However, it will be appreciated that a different anesthetizing "on-time" may be appropriate, as determined by the individual physician. After the stimulation-anesthetization, or ENS period, by employing any of the techniques known in the art, a conventional marrow aspiration commences, step 108, with little or no expected increase in the pain and discomfort experienced by the patient. Finally, in step 110, the ENS generator 31 is turned off. Now, the needle 22 may be removed from the patient to complete the procedure.

FIG. 5 depicts the method adjusting the ENS, step 106 in FIG. 4, in greater detail. In particular, the actual extraction may include a degree of feedback from the patient. The physician activates the ENS in step 104. The physician then asks the patient in step 120 if the electrical current is tolerated. If not, the voltage output is decreased in step 126, and step 120 is repeated. If the current is tolerated, the patient is asked in step 122 if he or she perceived anesthesia in the area of needle insertion. If not, the ENS output is increased in step 124 and step 120 is repeated. If anesthesia is experienced, the device is kept at this achieved voltage for approximately two minutes, step 128. Then the aspiration is conducted in step 108.

It should be understood that if the patient is to undergo a bone core procedure immediately after the aspiration procedure, the ENS generator 31 would be turned off. In this case, once the extraction step 108, is completed, the physician would retract the biopsy needle assembly a few millimeters, as discussed above, and would reinsert the needle, step 108, in a different location, and this time without a trocar inserted in the lumen of the needle shaft, for the purpose of conducting the bone coring procedure. If the coring procedure closely follows the aspiration procedure, it is expected that the electrical anesthesia will still be effective to attenuate the pain associated with the coring procedure.

Figure 6:
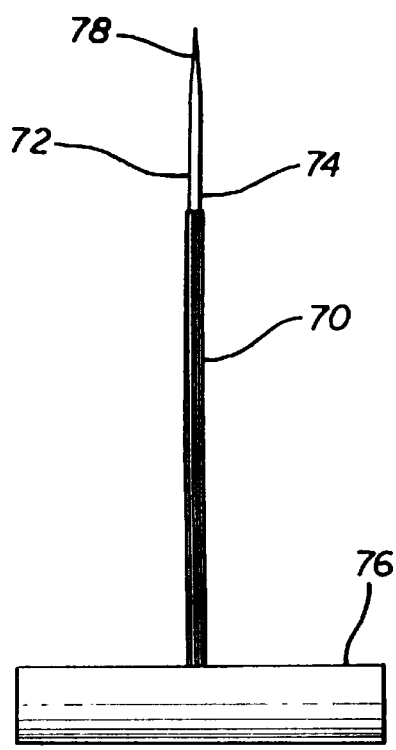
FIG. 6 is a plan view of the biopsy needle of the present invention wherein an electrically insulating sheath envelops a portion of the needle.

In accordance with another embodiment of the present invention, the electrical nerve stimulation is better concentrated towards the free end, or tip, of the needle, i.e. the location where the aspiration action commences and the pain is most acute. Accordingly, as shown in FIG. 6, a needle 72 similar to the one described in the previously described embodiments, includes a needle insulating sheath 70 in order to concentrate the anesthetizing current within the marrow cavity. This sheath 70 is a non-conducting tube that envelops the needle 72 and is fixed to the needle 72 via a frictional force, heat treatment, or any other acceptable means, such as an appropriate adhesive. The sheath 70 is comprised of any material that can both act as an electrical insulator and is safe for insertion into a patient, including, for example, the product manufactured under the trademark TEFLON®. As shown in the figure, when in place, the sheath extends from the end of the needle shaft 74 that is connected to the handle 76 down the needle shaft for any appropriate distance that is less than the entire length of the needle shaft 74. In the embodiment shown in FIG. 6, the sheath terminates at least three centimeters from the free end, or tip, 78 of the needle, to provide enough exposure of the conductive portion of the needle to the nerve fibers surrounding to effectuate meaningful electrical anesthesia.

Figure 7A:
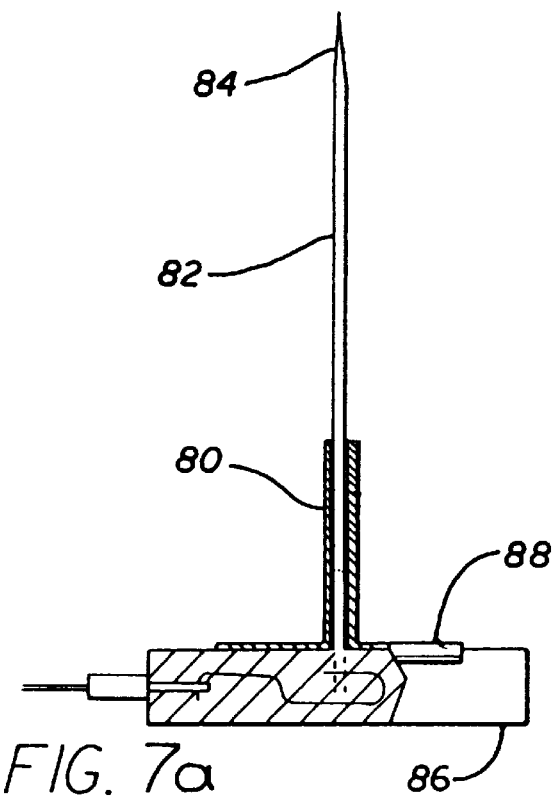
FIG. 7a is a cross-sectional view of another embodiment of the biopsy needle of present invention wherein the electrically insulating sheath slides along the outer surface of the needle.
Figure 7B:
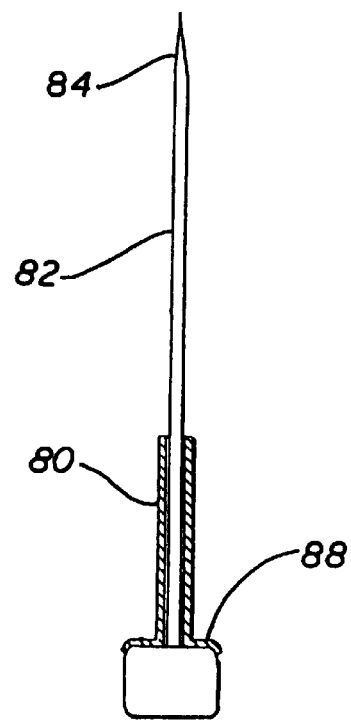

In the alternative embodiment shown in FIGS. 7a and 7b, the sheath 80, shown in cross-section, extends for approximately one third the length of the needle shaft 82 and has a molded base 88 which fits and removably secures to the needle assembly handle 86. For example, for one standard, adult size, Jamshidi® needle having a needle shaft of approximately nine to ten centimeters long, the sheath is only three centimeters in length so as not to interfere with the insertion of the needle 82 into the bone. However, it is understood that other sheath lengths relative to the length of the needle 82 used may be used. Once the needle is anchored, the physician can then slide the insulator 80 down the needle, through the tissue and against the bone surface. The wide sheath base 88 enables physician control of sheath 80 and prevents accidental loss of the sheath below the skin surface.

Having thus described an exemplary embodiment of the invention, it will be apparent that further alterations, modifications, and improvements will also occur to those skilled in the art. Further, it will be apparent that the present invention is not limited to use for bone marrow aspiration procedures but is likewise valuable for the attenuation of pain associated with bone coring procedures. Such alterations, modifications, and improvements, though not expressly described or mentioned above, are nonetheless intended and implied to be within the spirit and scope of the invention. Accordingly, the foregoing discussion is intended to be illustrative only; the invention is limited and defined only by the various following claims and equivalents thereto.

We claim:

1. A biopsy sampling system for attenuating the pain associated with the extraction of a sample of at least one of bone marrow and bone core from a patient through the patient's skin, soft tissue and bone, the system comprising:
   an electrically conductive biopsy needle configured to extract the sample; and
   an electrical nerve stimulator associated with the needle and configured to penetrate bone and to supply electrical stimulation to the patient along the needle so as to attenuate the pain during the extraction.

2. The system of claim 1, wherein the needle further includes:
   a handle having a plug receptacle that receives the first electrode of the electrical nerve stimulator, and
   a needle shaft comprising an electrically conductive cannula having one end connected to the handle and associated with the plug receptacle and an opposite, free end defining a needle tip adapted to bore the bone of the patient, the electrical nerve stimulator being configured to supply electrical stimulation to the patient along the cannula.

3. The system of claim 2, wherein the free end of the second electrode terminates in an electrode patch that releasably secures the positive electrode to the patient's skin.

4. The system of claim 2, further including an electrically insulating sheath enveloping the needle shaft and extending from the first end for a distance less than the length of the needle.

5. The system of claim 4, wherein the sheath frictionally engages the needle and terminates at least three centimeters from the free end of the needle shaft.

6. The system of claim 4, wherein the sheath is slidable along the entire length of the needle shaft to permit the sheath to slide into the patient after the needle shaft is fully inserted into the patient.

7. The system of claim 6, wherein the sheath is approximately one third of the length of the needle shaft.

8. The system of claim 2, wherein the energy delivery source is adapted to supply a current having an adjustable voltage, pulse rate and pulse width.

9. The system of claim 2, wherein the energy delivery source is portable and battery operated.

10. The system of claim 1, wherein the energy delivery source further includes an ammeter that provides a display of the amperage flowing through the patient.

11. A method for reducing the pain associated with the extraction of a sample of at least one of a bone marrow specimen and bone core specimen from a patient, wherein the system includes an electrically conductive biopsy needle that extracts the sample and an electrical nerve stimulator associated with the needle, the stimulator being further configured to supply electrical stimulation to the patient along the needle so as to attenuate the pain during the extraction, the method including:
    penetrating the biopsy needle into the bone within the patient;
    activating the electrical nerve stimulator so as to supply stimulation to the patient along the needle for a predetermined amount of time;
    extracting the sample from the patient into the biopsy needle assembly; and
    deactivating the electrical nerve stimulator.

12. The method of claim 11, wherein the activating of the electrical nerve stimulator further includes:
    increasing the frequency of the supply of the electrical nerve stimulator to a predetermined magnitude; and
    maintaining the supply to the patient for a predetermined amount of time.

13. The method of claim 12, wherein the predetermined amount of time for maintaining the supply of current is at least three minutes.

14. The method of claim 11, wherein the extracting of the sample from the patient into the biopsy needle assembly further includes:
    activating the electrical nerve stimulator at an initial output level;
    obtaining a first report from the patient relating to the patient's discomfort level coincident with the initial output level;
    decreasing the output level of the electrical nerve stimulator if the patient reports discomfort in the first report and returning to the obtaining of a first report;
    obtaining a second report from the patient relating to the level of anesthesia perceived by the patient;
    increasing the output level of the electrical nerve stimulator if the patient reports no perceived anesthesia and returning to the obtaining of a first report; and
    maintaining the electrical nerve stimulator output level for a preset period of time.

15. The method of claim 14, wherein the preset period of time is at least two minutes.

16. The method of claim 11, wherein the extracting of the sample from the patient into the biopsy needle assembly further includes the focusing of the electrical current to a portion of the needle assembly that communicates with the area of the bone to be aspirated.

17. A biopsy sampling system for attenuating the pain associated with the extraction of a sample of at least one of bone marrow and bone core from a patient through the patient's skin, soft tissue and bone, the system comprising:

an electrically conductive biopsy needle configured to extract the sample; and an electrical nerve stimulator associated with the needle and configured to supply electrical stimulation to the patient along the needle so as to attenuate the pain during the extraction;

wherein the electrical nerve stimulator includes an adjustable energy delivery source, a first electrode associated with the needle and a second electrode having a free end that removably engages the skin of the patient.

* * * * *